(12) United States Patent
Malyarov et al.

(10) Patent No.: US 7,951,329 B2
(45) Date of Patent: May 31, 2011

(54) ROTARY LUMINOMETER

(75) Inventors: Ilya Malyarov, Livingston, NJ (US); Thomas Palmieri, Paramus, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1450 days.

(21) Appl. No.: 10/813,575

(22) Filed: Mar. 31, 2004

(65) Prior Publication Data

US 2005/0220669 A1    Oct. 6, 2005

(51) Int. Cl.
*G01N 35/02* (2006.01)
(52) U.S. Cl. .............. 422/64; 422/63; 436/47; 436/172; 356/244; 356/246; 356/440
(58) Field of Classification Search .............. 422/52, 422/63–65, 82.05, 99–104; 436/47, 172; 356/244, 246, 440
See application file for complete search history.

(56) References Cited

U.S. PATENT DOCUMENTS

| | | | | |
|---|---|---|---|---|
| 3,852,599 A | * | 12/1974 | Smith | 250/328 |
| 4,755,055 A | * | 7/1988 | Johnson et al. | 356/440 |
| 4,826,660 A | * | 5/1989 | Smith et al. | 422/82.05 |
| 5,316,726 A | * | 5/1994 | Babson et al. | 422/65 |
| 5,384,094 A | * | 1/1995 | Schacher | 422/64 |
| 5,445,794 A | * | 8/1995 | Wihlborg | 422/63 |
| 5,658,532 A | * | 8/1997 | Kurosaki et al. | 422/64 |
| 5,885,529 A | * | 3/1999 | Babson et al. | 422/65 |
| 6,335,166 B1 | * | 1/2002 | Ammann et al. | 435/6 |

* cited by examiner

*Primary Examiner* — P. Kathryn Wright

(57) ABSTRACT

A rotary luminometer subsystem presents test vessels to a detection mechanism to be read as part of the automated immunoassay analyzer system. The rotary luminometer provides a read station separate from that of the transportation element of the luminometer. Within the read station, a housing and shield eliminates light leakage from the sample under test. In addition, the read station regulates the intensity of the light by providing an attenuation capability.

17 Claims, 5 Drawing Sheets

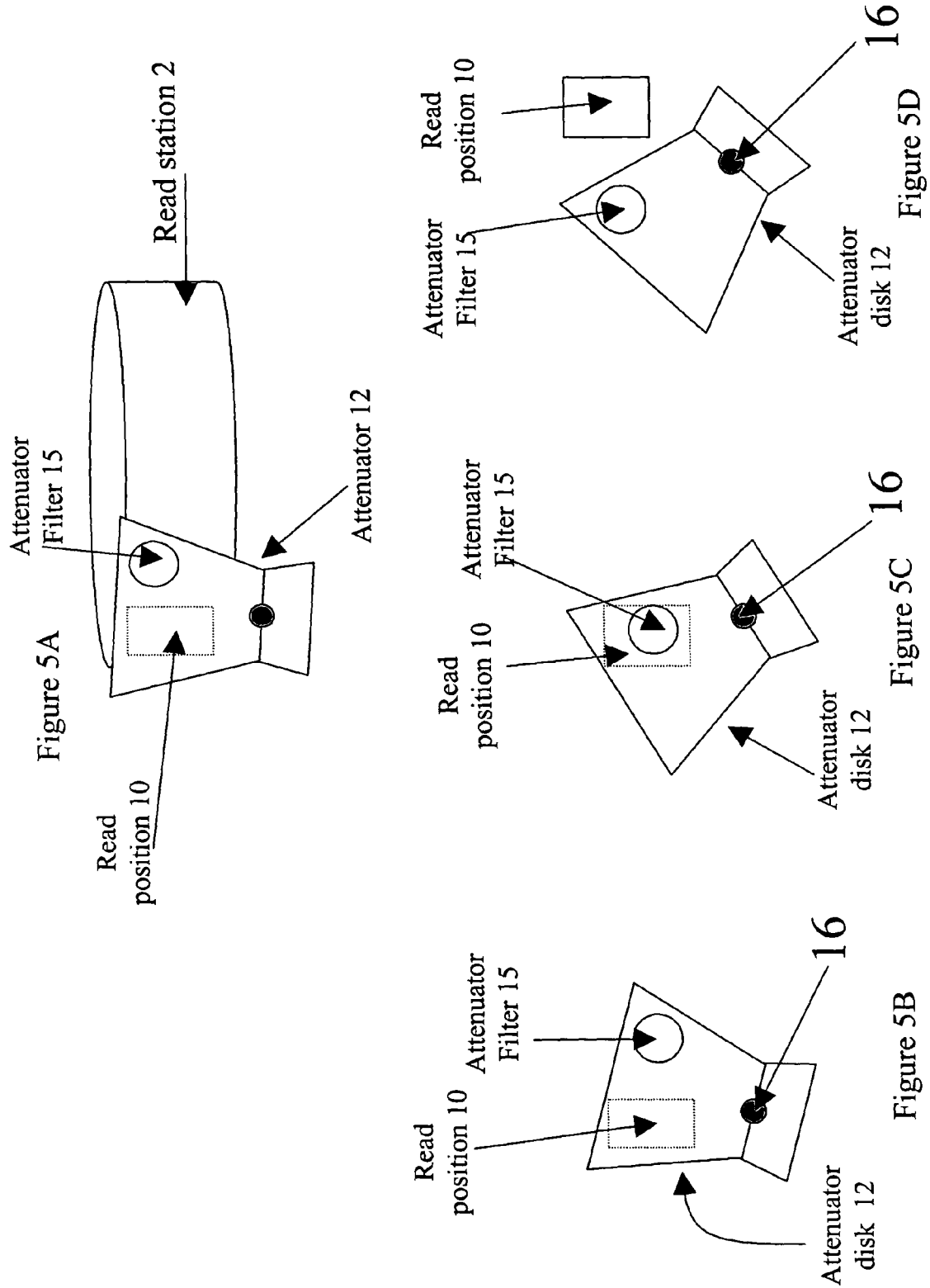

ROTARY LUMINOMETER

BACKGROUND OF THE INVENTION

1. Field of the Invention

The present invention generally relates to a luminometer subsystem within an automated immunoassay analyzer used to quantify the analyte obtained from a test sample and, more particularly, to a subsystem that presents the reaction vessel to a detection mechanism, reads the varying light intensities that correspond to a concentration of a sample analyte to be quantified, and disposes of the analytical element and substrate after completion of a measurement.

2. Background Description

Automated immunoassay analyzers are being manufactured that allow a computer controlled system to analyze the amount of analyte in a sample such as blood, plasma or urine. To quantify the results, the sample is subjected to a myriad of complex processes that may include sample dilution, adding reagents, incubating, agitating, washing and reading of the sample. Reading of the sample has been performed previously using a detection mechanism (e.g., chemiluminescent) that measures the intensity of the light and calculates the related value of the analyte. See for example U.S. Pat. Nos. 5,885,530; 5,885,529; 5,723,092; 5,721,141; 5,632,399; 5,318,748; 5,316,726; 5,258,309; 5,098,845; 5,084,240; and 4,639,242; all of which are herein incorporated by reference.

Automated immunoassay analyzers have traditionally performed testing of samples in a serial manner. That is, a sample is presented to the analyzer and it progresses step by step through the various processes until completion. While this first sample is progressing through the analyzer, all other samples follow. That is, there is a single path through currently available analyzers. Once the sample reaches the luminometer subsystem, it is then read using a detection mechanism while on the transportation element. This means the readings must be performed in a serial fashion on a first come first serve basis, see for example, Carey et al. (U.S. Pat. No. 5,637,275) which is herein incorporated by reference. Removing the test vessel from the transportation apparatus and placing it in a separate read station to be read at intervals appropriate to the individual assays would be an advantage over presently available systems.

Typically, the test vessel is read while still on the transportation system. Small shutters are lowered around the vessel to be read to attempt to isolate the vessel under test and to attempt to eliminate cross talk from the neighboring vessels. It would be desirable to improve the isolation of the vessel under test while the reading is performed.

In addition, current detection mechanisms operate in a set cycle time for each step of the process. That is, the transportation element moves within a fixed time slot. As such, samples that are being transported through the system are presented to the detection mechanism after a fixed length of time. This does not allow optimization for the individual assay. This may cause some variances in the accuracy of certain assays within the automated immunoassay analyzer.

SUMMARY OF THE INVENTION

It is an object of this invention to provide an improved analyte detection station for an automated immunoassay analyzer, which detects bound analyte by, for example, chemiluminescence, phosphorescence, fluorescence, colorimetric change, or other means.

It is another object of this invention to provide an analyte detection station that has a separate detector section and transport section, with a transfer device that moves vessels between the two sections.

It is yet another object of the invention to provide an analyte detection station with a shielded detector section whereby radiant energy (e.g., light) from sources other than the vessel under test (e.g., crosstalk from adjacent vessels or radiant energy from the ambient environment) is shielded from the detector during measurement.

It is still another object of the invention to provide a detection station for an automated immunoassay analyzer which allows for a variable and optimizable time period between a time when a chemical agent which reacts with bound analyte in a vessel is added to the vessel and a time when the amount of bound analyte is determined using the detector.

It is another object of the invention to provide an improved analyte detection station for an automated immunoassay analyzer which allows different tests performed in different vessels which are transported together on a transport section to be maintained for varying and different amounts of time in the transport section before being transferred to the detector for detection.

It is also an object of the invention to provide a detection station that reduces cross talk radiant light interference from other vessels in immunoassay analyzer.

According to the invention, an analyte detection station used in an automated immunoassay analyzer includes a transport device or mechanism for transporting a plurality of vessels (e.g., tubes, etc.) under investigation to a detector which preferably detects radiant energy (e.g., preferably chemiluminescence generated when a bound analyte cleaves a chemical substrate) or a color change (a color change detection would require a means for illuminating the vessel which is being read) that is indicative of the amount of bound analyte within the vessel (thereby providing a reading of the amount of analyte under investigation in the sample being tested). The detector is maintained in a housing separate from the transport device or mechanism, and a transfer device is used to individually transfer vessels from the transport device or mechanism to be presented to the detector. Preferably, the housing includes a rotary portion which moves the individual vessel from a point of transfer in the housing to a position in front of the detector where the vessel is completely shielded from radiant energy from the surrounding environment (e.g., stray light). In this way, the reading made by the detector accurately reflects only the radiant energy (or color change) in the vessel, and thereby permits highly accurate determination of the analyte of interest in the sample under investigation. The housing is also preferably configured to allow easy disposal of vessels after the detector has made a reading.

Furthermore, the analyte detection station of the present invention permits performing analyte detection in a randomized fashion, as opposed to a serial, one after the other, fashion. This allows for varying the time period between adding chemical reagents to the test vessel that interact with bound analyte to produce radiant energy or color change, and the time when the individual vessels are presented to the detector for analysis. In this way, the time duration for the type of test being performed can be optimized. This is accomplished by having the transport section separate from the detector section, whereby transfer from the transport section to the detector section occurs under the direction of a controller which effects the transfer at an interval that is preferably optimized for the test being performed, as well as in light of the other tests which are currently on the transport device.

BRIEF DESCRIPTION OF THE DRAWINGS

The foregoing and other objects, aspects and advantages will be better understood from the following detailed description of a preferred embodiment of the invention with reference to the drawings, in which:

FIG. 5A shows a side view of the attenuator disk relative to the read station.

FIG. 5B shown the attenuator disk in the dark position.

FIG. 5C shows the attenuator disk in the attenuated position.

FIG. 5D shows the attenuator disk in the unattenuated position.

DETAILED DESCRIPTION OF A PREFERRED EMBODIMENT OF THE INVENTION

Figure 1:
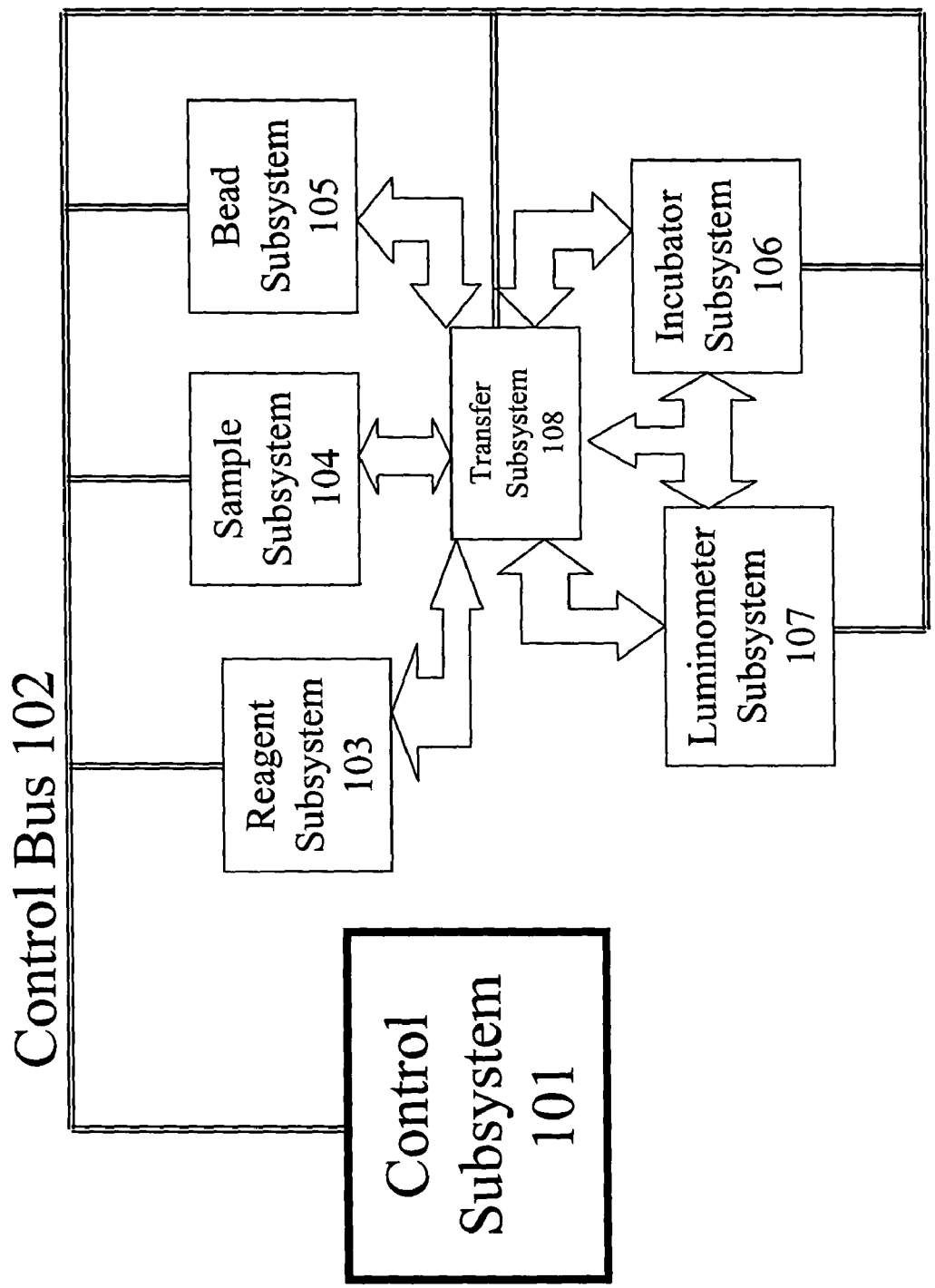
FIG. 1 is an overview of an automated immunoassay analyzer.

Referring now to the drawings, and more particularly to FIG. 1, which shows an automated immunoassay analyzer as a complex system with numerous subsystems that allow the tests to be performed without the continuous monitoring and intervention of a technician. The technician selects the tests to be performed for each sample and enters this information via the control subsystem 101. The control subsystem 101 manages the other subsystems by sending command and control information via the control bus 102. Samples of biological material (e.g., blood, urine, plasma, etc.) are placed by the technician in the sample subsystem 104. The samples within the sample subsystem 104 can be diluted prior to making measurements or can be tested in the undiluted state depending on direction from the control subsystem 101. The bead subsystem 105 adds the appropriate substrate having a bound "analyte binding compound" to the test vessel. Preferably, the substrate is present in the form of one or more beads having adhered thereto a compound for binding the analyte of interest from the sample under test (e.g., via antigen-antibody binding, etc.). The reagent subsystem 103 adds the specified reagent to the test vessel. The selection of bead and reagent for each sample is managed by the control subsystem 101 based on the type of test to be performed on each sample. These subsystems include identification capabilities such as, for example, bar code readers or RF readers that read the bar code or RFID identification information on the reagent containers, bead containers and sample tubes to ensure the correct components are added to each test vessel for testing. The test vessel is moved within the analyzer via the transfer subsystem 108. Once the selected components are added to the test vessel, the incubator subsystem 106 incubates and agitates the test vessel as managed by the control subsystem 101. The incubator operation is described in more detail in the co-pending application, Multipath Access System For Use In An Automated Immunoassay Analyzer, U.S. patent application Ser. No. 10/813,604; however, it should be understood that this invention can be employed in numerous incubator and non-incubator applications depending on the design requirements for the vessel transportation assembly. The test vessel is then washed and transferred to the luminometer subsystem 107 via the transfer subsystem 108. The luminometer subsystem 107 selects the test vessel and presents it to the detection mechanism. After the read operation is performed, the test vessel is discarded.

Figure 2:
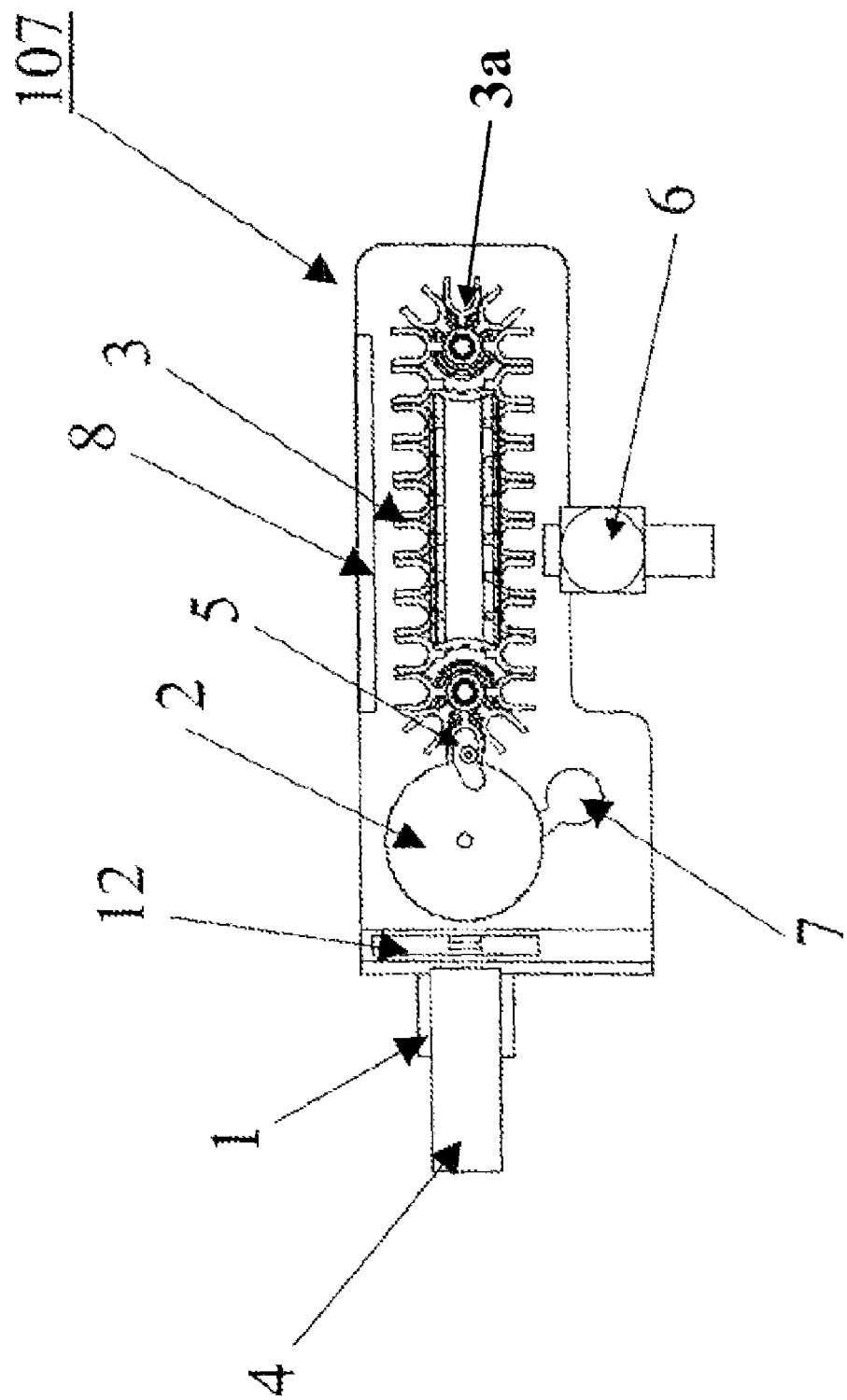
FIG. 2 is a block diagram of the major elements of the luminometer subsystem.

This invention is directed to the luminometer subsystem 107. The luminometer subsystem 107 can be employed in a wide variety of automated immunoassay analyzers, and should be applicable to any analyzer which requires reading of radiant energy or color change to identify the amount of a particular compound with a vessel. Furthermore, it should also be understood that aspects of this invention may be employed in automated immunoassay analyzers or chemical analyzers which detect phosphorescence, fluorescence, color change, etc. FIG. 2 shows a more detailed view of luminometer subsystem 107. The transfer subsystem 108 (shown in FIG. 1) transfers the test vessels to the luminometer subsystem 107 after a wash operation is performed at one or more wash stations 6. The transfer subsystem 108 loads the test vessels 5 onto the luminometer belt 3. The luminometer belt 3 rotates in either a clockwise or counterclockwise direction as directed by the control subsystem 101 of the automated immunoassay analyzer. A substrate and/or chemical reagent is added to the test vessel 5 and the test vessel 5 is moved along the luminometer belt 3 and shaken by the agitator 8. The agitator 8 is described in more detail in the co-pending application, Vessel Agitator Assembly, U.S. patent application Ser. No. 10/813,576; however, it should be understood that this invention can be used in combination with a variety of devices that agitate vessels that are present in vessel transportation assemblies. In short, preferably as the vessels pass by the bumps on the agitator 8, the vessels contact the agitator 8 and are essentially "bumped" or agitated. When commanded by the control subsystem 101, the test vessel 5 is transferred to the read station 2. While in the read station 2, the test vessel is read by the detection mechanism 4 and then discarded to the exit chute 7. In order to protect the detection mechanism 4 from exterior light, the detection mechanism 4 is connected to the read station 2 through a sealed sleeve 1. The sleeve 1 allows the optional attenuation disk 12 to move relative to the read station 2 while preventing exterior light from entering the detection mechanism 4.

One of the important advantages of the present invention is that the read station 2 and luminometer belt 3 are separate. This allows each of the plurality of vessels loaded into the luminometer subsystem 107 to remain on the belt for variable lengths of time. That is, in the preferred embodiment, the test vessels are not required to be serially fed one after another to the read station 2. By using the preferred embodiment that comprises separate mechanisms for transporting the test vessels and for reading the test vessels, test vessels can be agitated while one of the test vessels is being read. Rather, based on the test being performed in a particular test vessel, the test vessel may remain on the belt for shorter or longer time periods. Some tests may optimally require longer periods between the time when a chemical agent that will be cleaved by bound material on the bead to produce chemiluminescence, phosphorescence, fluorescence or color change is added to the vessel relative to the time when the detection mechanism 4 detects the chemiluminescence, phosphorescence, fluorescence or color change. In addition, some tests may be prioritized for patient care reasons, and will proceed at a faster rate from the luminometer belt 3 to the detection mechanism 4. Thus, preferably, the control subsystem 101 is programmed to control the order of when a test vessel 5 is transferred between the luminometer belt 3 to the read station 2, and it can accomplish this control by tracking the location of the test vessel 5 in the luminometer belt 3. Hence, every test vessel 5 essentially has its own timed interval in the luminometer belt 3, and this timed interval can be controlled based on the test being performed, the other test vessels 5 that are present in the luminometer belt 3, as well as by a prioritization scheme or according to other directives.

While FIG. 2 shows the transport device or mechanism as an oval shaped luminometer belt 3, having a plurality of vessel receptacles 3a each for receiving a vessel 5. It should be understood that other transport devices or mechanisms, such as belts, etc., could be used. In addition, the configuration for the transport belt does not need to be in an oval. An important feature for the preferred embodiment, however, is that the test vessels can be moved backwards and forwards in a controlled fashion at a controlled time interval to be presented to the read station 2.

Figure 3:
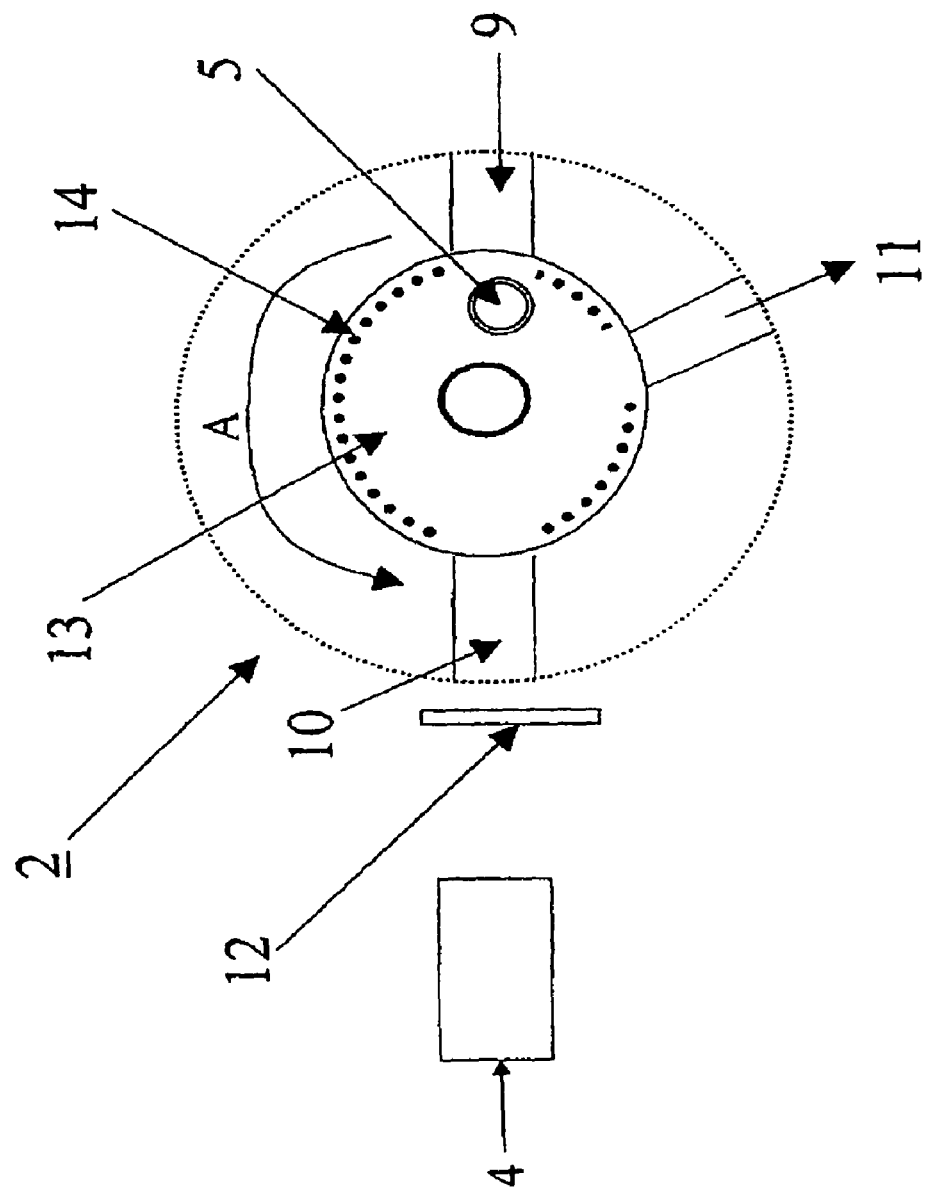
FIG. 3 is an illustration the luminometer read station.

FIG. 3 shows the progress of the test vessel 5 within the read station 2. The test vessel 5 enters the read station 2 from the luminometer belt 3 at entry position 9. The test vessel 5 is preferably rotated in the counterclockwise direction shown by arrow A around to read position 10. While at read position 10, the test vessel 5 is read by the detection mechanism 4 (e.g., a Photomultiplier Tube (PMT) in the preferred embodiment). The detection mechanism 4 is protected from exterior light leakage by a sleeve 1 (shown in FIG. 2), a housing 13 and a shield 14 that is part of the luminometer subsystem.

Another important advantage of the invention having a separate read station 2, and luminometer belt 3, is the improved ability to shield the test vessel 5 undergoing detection. This prevents crosstalk from adjacent vessels or ambient radiant energy from adversely impacting on the measurement. The detection mechanism 4 (e.g., Photomultiplier Tube (PMT) is highly sensitive to exterior light.

Although FIG. 3 shows the read station 2 rotating in the counterclockwise direction, it is understood that the read station 2 may rotate in either the clockwise or counter clockwise direction.

Figure 4:
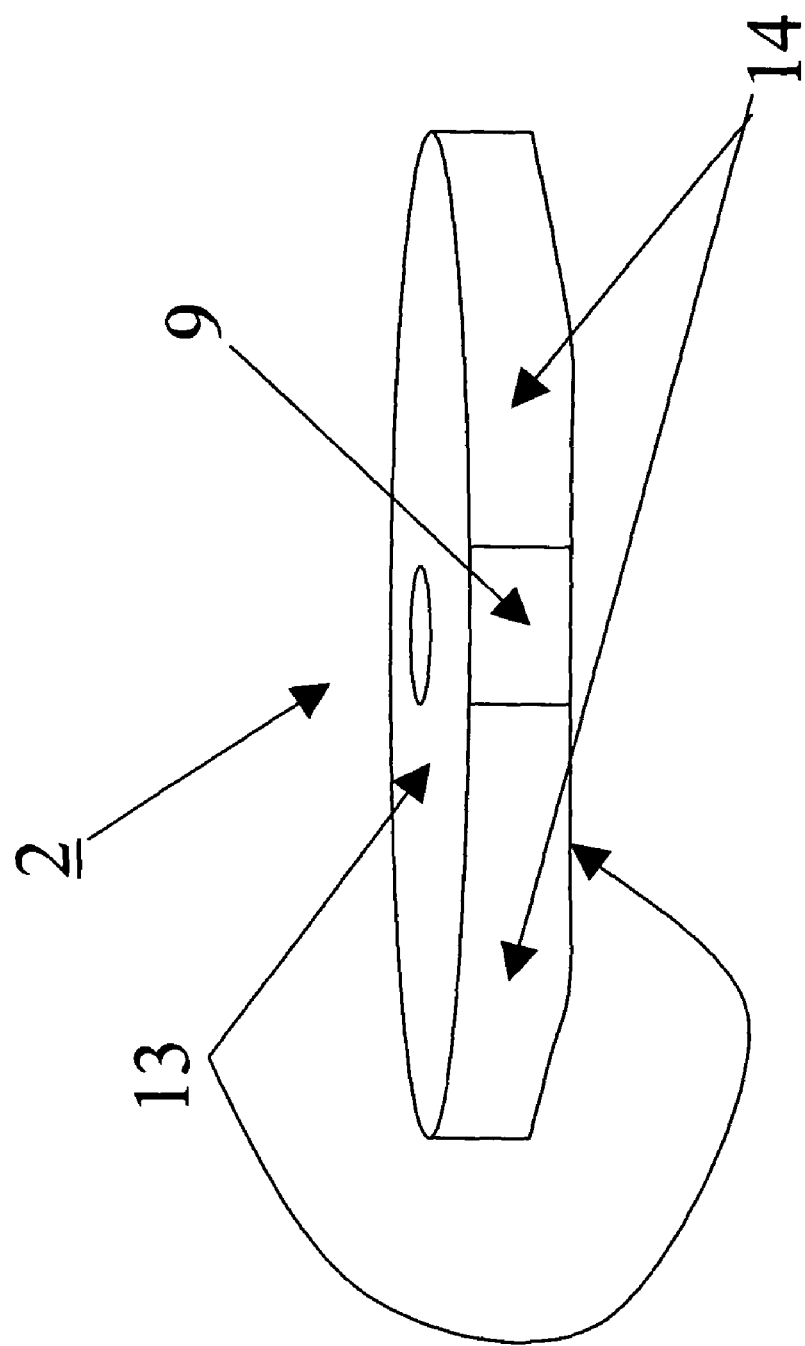
FIG. 4 is a side view of the luminometer read station.

FIG. 4 shows a side view of the read station 2. The housing 13 is considered to be the top and bottom (not shown) of the read station 2. The shield 14 is a wall that extends around the read station 2 and is open only at the entry position 9, read position 10 and exit position 11. The shield 14 prevents leakage of the sample radiation outside the read station 2. In addition, the shield 14 also isolates the test vessel under test from the other vessels to prevent crosstalk during measurement by the detection mechanism 4. The read station 2 provides a means for biasing the test vessel 5 under test toward the external edge of the read station 2 while at read position 10. That is, the bottom (not shown) of the read station 2 housing 13 may be angled down or other similar means such that each test vessel 5 is positioned at exactly the same distance from the detection mechanism 4 during each reading.

Another embodiment of the invention is to provide a means for measuring the PMT dark counts (i.e., signals that register in the absences of light). This can be performed when the read station 2 is in the 'dark' position. That is, when the read station 2 rotates approximately halfway between the the entry position 9 and the read position 10. This measurement can be performed with a test vessel 5 within the read station 2 or when there is no test vessel 5 within the read station 2.

An optional embodiment of the invention is to provide an attenuation means as an attenuation disk 12 between the read station 2 and the detection mechanism 4. Referring to FIG. 5A, an attenuator disk 12 can preferably be mounted between the read station 2 and the detection mechanism 4. The location of the optional attenuation disk 12 is shown in FIG. 2. The attenuator disk 12 is shown as a trapezoidal shaped element that rotates around a pin 16, although other shapes may be use. The attenuator disk 12 is comprised of a solid material that does not allow radiant light to pass through. An attenuator filter 15 is located on one side of the attenuator disk 12. The attenuator disk 12 rotates around pin 16 to allow the attenuator disk 12 to be in one of three possible conditions. Specifically, FIG. 5B shows the attenuator disk 12 in the 'dark' condition. That is, the solid material of the attenuator disk 12 is in front of the read position 10 of the read station 2 such that the detection mechanism 4 receives no light from the test vessel allowing the automated immunoassay analyzer to measure electrical background signal which can be subtracted from the measured signal t obtain a more accurate reading. FIG. 5C shows the attenuation disk 12 in the 'attenuated' state relative to read position 10 where the detection mechanism 4 can receive signals through a neutral-density filter. FIG. 5D shows the attenuator disk 12 in the 'unattenuated' state relative to read position 10 such that the detection mechanism 4 receives the full signal produced in the test vessel 5. However, another embodiment of the invention would be to have an attenuation means that does not require the 'dark' position.

The duration of time in which the test vessel 5 is present in the read station 2 at read position 10 is preferably managed by the control subsystem 101 and is dependent upon the specific test being performed. It may be desirable to present the same sample to the detection mechanism for multiple read cycles. Once the analyte is read, the test vessel 5 is discarded at the exit position 11. The exit position 11 is preferably located approximately 110° from the read position 10 to prevent light leakage from the test vessel 5.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. An analyte detection station for an automated immunoassay analyzer, comprising:
   a read station rotatable between an entry position and a read position;
   a detector coupled to said read station at said read position for detecting radiant energy or color emanating from said read station;
   a wash station that performs a wash operation;
   a transport device that receives vessels from said wash station and for transporting a plurality of vessels from said wash station through a defined path, each of said vessels containing at least one bound analyte and at least one compound for emitting radiant energy or color, and for transferring one of said plurality of vessels from said defined path into said read station at said entry position;
   wherein said read station is capable of rotating a transferred vessel from said entry position to said read position independently of motion of said plurality of vessels through said defined path.

2. The analyte detection station for an automated immunoassay analyzer as recited in claim 1, wherein said detector detects chemiluminescence.

3. The analyte detection station for an automated immunoassay analyzer as recited in claim 1, wherein said detector detects fluorescence.

4. The analyte detection station for an automated immunoassay analyzer as recited in claim 1, wherein said detector detects phosphorescence.

5. The analyte detection station for an automated immunoassay analyzer as recited in claim 1, wherein said read station includes a shield for shielding said transferred vessel from external radiant energy when it is transferred to said read position when said detector is detecting said radiant energy.

6. The analyte detection station for an automated immunoassay analyzer as recited in claim 5, wherein said read station biases the vessel in said read station a set distance from the detector when in the read position.

7. The analyte detection station for an automated immunoassay analyzer as recited in claim 5, wherein said read station operates by rotational movement.

8. The analyte detection station for an automated immunoassay analyzer as recited in claim 5, wherein said read station further moves said transferred vessel to a disposal position for disposing of said vessel after it moves said vessel to said read position.

9. The analyte detection station for an automated immunoassay analyzer as recited in claim 8, wherein said read station operates by rotational movement.

10. The analyte detection station for an automated immunoassay analyzer as recited in claim 1, wherein said transport device is a continuous carousel, chain or belt which includes a plurality of vessel receptacles for receiving each of said plurality of vessels.

11. The analyte detection station for an automated immunoassay analyzer as recited in claim 10, wherein said continuous chain or belt can receive vessels in said vessel receptacles at a plurality of locations.

12. The analyte detection station for an automated immunoassay analyzer as recited in claim 1, further comprising an attenuation means for attenuating light signals entering said detector from said read station.

13. The analyte detection station for an automated immunoassay analyzer as recited in claim 12, wherein said attenuation means is located between said read station and said detector, wherein said attenuation means can be set at any one of at least two attenuation positions.

14. The analyte detection station for an automated immunoassay analyzer as recited in claim 13, wherein said any one of at least two attenuation positions include: an unattenuated position where light from said vessel can be read directly by said detector, and an attenuated position where light from said vessel can be read by the detector through a neutral density filter.

15. The analyte detection station for an automated immunoassay analyzer as recited in claim 12, wherein said attenuation means is located between said read station and said detector, wherein said attenuation means can be set at any one of at least three attenuation positions.

16. The analyte detection station for an automated immunoassay analyzer as recited in claim 15, wherein said any one of at least three attenuation positions include: an unattenuated position where light from said vessel can be read directly by said detector, a dark position where no light from said vessel can be read by said detector, and an attenuated position where light from said vessel can be read by the detector through a neutral density filter.

17. The analyte detection station for an automated immunoassay analyzer as recited in claim 1, further comprising means for measuring dark counts for determining ambient light levels within the detector.

* * * * *